US005537095A

United States Patent [19]
Dick et al.

[11] Patent Number: 5,537,095
[45] Date of Patent: Jul. 16, 1996

[54] INCONTINENCE DETECTION DEVICE

[75] Inventors: Bonnie R. Dick, Cincinnati; Robert T. Duke, Milford, both of Ohio; Eugene E. Osborne, Florence, Ky.; Steven P. Sable, Brockport, N.Y.; Thomas E. Scott, Indianapolis, Ind.; Chas Taverner, West Amherst, N.Y.

[73] Assignee: Hill-Rom Company, Inc., Batesville, Ind.

[21] Appl. No.: 145,767

[22] Filed: Oct. 29, 1993

[51] Int. Cl.$^6$ ................................................. G08B 21/00
[52] U.S. Cl. .......................... 340/605; 128/886; 340/573; 340/604
[58] Field of Search .................................... 340/604, 605, 340/573, 603, 286.07, 666; 200/61.05; 128/886; 73/40

[56] References Cited

U.S. PATENT DOCUMENTS

| | | |
|---|---|---|
| 1,772,232 | 8/1930 | Guilder . |
| 2,127,538 | 8/1938 | Seiger . |
| 2,644,050 | 6/1953 | Seiger . |
| 2,668,202 | 2/1954 | Kaplan . |
| 2,726,294 | 12/1955 | Kroening et al. . |
| 2,907,841 | 10/1959 | Campbell . |
| 3,199,095 | 8/1965 | Ashida . |
| 3,971,371 | 7/1976 | Bloom . |
| 4,069,817 | 1/1978 | Fenole et al. ................ 200/61.05 |
| 4,106,001 | 8/1978 | Mahoney ........................ 340/604 |
| 4,163,449 | 8/1979 | Regal ............................ 200/61.05 |
| 4,191,950 | 3/1980 | Levin et al. ..................... 340/604 |
| 4,212,295 | 7/1980 | Snyder .......................... 340/573 |
| 4,228,426 | 10/1980 | Roberts ......................... 340/573 |
| 4,347,503 | 8/1982 | Uyehara ......................... 340/604 |
| 4,539,559 | 9/1985 | Kelly et al. ..................... 340/573 |
| 4,965,554 | 10/1990 | Darling ......................... 340/604 |
| 5,081,422 | 1/1992 | Shih ............................ 340/605 |
| 5,086,291 | 2/1992 | Schwab, Jr. ..................... 340/604 |
| 5,137,033 | 8/1992 | Norton .......................... 340/573 |
| 5,144,284 | 9/1992 | Hammett ........................ 340/573 |
| 5,291,181 | 3/1994 | De Ponte ....................... 340/604 |

FOREIGN PATENT DOCUMENTS

| 2145859 | 4/1985 | United Kingdom .................. 340/604 |
|---|---|---|

*Primary Examiner*—Brent A. Swarthout
*Attorney, Agent, or Firm*—Barnes & Thornburg

[57] ABSTRACT

An incontinence detection device comprising a pad with a plurality of circuits. The circuit conductors are spaced on the pad, with each of the circuits defining a linear dimension across a respective pair of the circuit conductors. The linear dimension has a correlation to a predetermined liquid volume of an incontinent event desired to be detected. A controller applies voltage from a power source to and checks continuity of the spaced circuits and totals the circuits. The controller indicates to a care provider that an incontinent event has occurred at a certain minimum liquid volume.

21 Claims, 4 Drawing Sheets

INCONTINENCE DETECTION DEVICE

FIELD OF THE INVENTION

This invention relates generally to patient monitoring devices such as those used in hospitals and nursing homes, and more particularly to a device for placement upon a hospital bed for detecting the presence of a patient incontinent event.

BACKGROUND OF THE INVENTION

Various devices have been proposed for detecting the presence of a hospital patient incontinent event, i.e., the presence of urine. Pads have been developed which employ a single electrical circuit within the pad, with a number of moisture-sensitive electrical conductors electrically connected in parallel to the voltage source applied to the circuit. One or more of the moisture-sensitive electrical conductors, upon being moistened by urine, complete the electrical circuit. An alarm has traditionally been wired into the circuit, with the moisture-sensitive conductors being positioned between the alarm and power supply. Hence, when a patient incontinent event occurs, the alarm is activated, apprising a caregiver that the patient should be attended to.

The single circuit type of device which has a number of moisture-sensitive conductors electrically connected in parallel with the voltage source of the device can take one of two forms. One form is as illustrated in Norton U.S. Pat. No. 5,137,033 wherein electrical conductors, for example foil strips, are spaced through the thickness of the pad with fabric separating the strips, such that when the pad is moistened by urine through its depth the circuit becomes complete from the top to the bottom of the pad through the pad.

Another type of device which similarly employs a single circuit with a number of moisture-sensitive electrical conductors electrically connected in parallel to the voltage source of the device is the type which utilizes a single electrical conductor woven back and forth through the pad but within a uniform horizontal plane of the pad. In this type of device the voltage source is applied to the two ends of the conductor, but the conductor is an "open" circuit as there is a break in the conductor somewhere along its path. The conductor is woven such that adjacent points of the electrical conductor are within, for example, approximately one inch of each other. When fabric between adjacent points of the conductor becomes moistened the circuit becomes complete. This type of device is shown, for example, in Kelly et al U.S. Pat. No. 4,539,559.

In neither of these two types of devices, that is, the type employing moisture-sensitive conductors spaced through the pad thickness, or the type having conductors spaced across the width and length of the pad in a uniform plane, is the device able to discriminate between incontinent events of varying volumes. That is to say, an incontinent event, of any liquid volume, as long as the urine therefrom is positioned in the appropriate position on the detecting pad, will activate the device and hence notify the caregiver that the patient is to be attended to. Thus, the caregiver is notified that the patient needs to be attended to, whether the incontinent event is 30cc's or 300cc's, the former ordinarily not requiring immediate care, while the latter may do so. Accordingly, these types of devices are subject to so-called "nuisance" readings, wherein a very small incontinent event will trigger the device indicating that the patient requires care by a caregiver, whereas in fact it would not be paramount that the patient receive care at that time.

With respect to the type of device employing the moisture-sensitive conductors through the thickness of the pad, varying the lateral spacing of the conductors essentially has no effect on the "resolution" of the device, as long as the urine, no matter how small the volume, is centered over one of the conductors. Therefore, the device could be triggered by either a 30cc event or a 300cc event. With respect to the other type of device employing the moisture-sensitive conductors within a common plane, increasing the linear distance between adjacent points on the conductor will desirably decrease the resolution of the device so as to avoid nuisance alarms; however, as in the former device there is no means by which to discriminate for varying volumes of the incontinent event.

SUMMARY OF THE INVENTION

It has therefore been an objective of the present invention to provide an incontinence detection device which has the ability to screen or discriminate those incontinent events which are of a liquid volume that would cause the device to generate a nuisance alarm, so that the device would not generate an alarm signal when the incontinent event is less than a pre-determined minimum threshold level.

It has been another objective of the present invention to provide an incontinence detection device which can provide a care provider with the approximate liquid volume of the patient incontinent event.

In accordance with the stated objectives of the present invention and a preferred embodiment thereof, the incontinence detection device of the present invention is for detecting a patient incontinent event and corresponding liquid volume of the event. The device comprises a pad with a plurality of electrical circuits on the pad. The circuits are spaced on the pad, with each of the circuits defining a linear dimension across a respective one of the circuits. The linear dimension has a correlation to a predetermined liquid volume of an incontinent event desired to be detected. The invention provides a power source, and a controller for applying voltage from the power source to and checking continuity of the spaced circuits and totaling the number of shorted circuits. When an incontinent event occurs the controller indicates to a care provider that an incontinent event has occurred, and the resulting liquid volume of that event. The predetermined liquid volume corresponds to the liquid volume of a minimum threshold incontinent event desired to be detected.

In one embodiment of the device of the present invention, the spaced circuits are overlapped, and the linear dimension across respective ones of the circuits is about 7.5 in., which corresponds to a predetermined liquid volume of about 100cc's.

In another embodiment of the present invention, the spaced circuits are contiguous, and the linear dimension across respective ones of the circuits is about 2.5 in., which corresponds to a predetermined liquid volume of about 20cc's.

The pad of the incontinence detection device of the present invention can be either disposable or reusable. If disposable, the circuits can be fabricated of either metallized mylar strips, conductive ink or conductive glue. If the pad included in the detecting device is a reusable pad, the circuits can be fabricated of either metallized mylar strips, conductive ink, conductive glue or metallized thread.

The invention further provides for verifying the electrical connection between the incontinence detection device and a connector for connecting a voltage source to the device. In this form the invention comprises an incontinence detection pad having a plurality of spaced conductors, each of the conductors having a contact and one of the conductors having a pair of contacts, a connector having a plurality of pins for connection to the pad, a power source for applying voltage to the pins, and a controller for sequentially applying power source voltage to each pin and checking for continuity to adjacent pins. When voltage is applied by the controller to the connector pin corresponding to one of the pair of contacts and when continuity is noted by the controller at the other of the pair of contacts, an electrical connection between the pad contacts and the controller pins has been achieved and is thus verified by the controller.

For an incontinence detection apparatus comprising a pad having n spaced conductors and a connector for connection to the pad having m pins, where n ≠ m, the invention provides for initializing the connector pins relative to the pad contacts. When voltage is applied by the controller to the connector pin corresponding to one of the pair of contacts and continuity is noted by the controller at the other of the pair of contacts, the controller notes which connector pin corresponds to the conductor with the pair of contacts and then notes the relationship of the remaining connector pins to the remaining conductors.

The incontinence detection device of the present invention provides numerous advantages over prior art devices. First, so-called nuisance alarms are eliminated, as the resolution of the pad can be adjusted to indicate a desired minimum threshold incontinent event. Second, the incontinence detection device of the present invention has the capability of providing a care provider with the information of the volume of the incontinent event, which is useful to the care provider in determining whether immediate patient care is required or, for example, if the pad is full of urine and needs to be replaced. Third, the pad, connector and controller of the device of the present invention allow for less than exact manual placement of connector onto pad yet automatically verify that an electrical connection between connector and pad has been made as well as determine the relationship of connector pins to pad conductor contacts.

These and other objectives and advantages of the present invention will become more readily apparent during the following detailed description taken in conjunction with the drawings herein, in which:

DETAILED DESCRIPTION OF THE INVENTION

Figure 1:
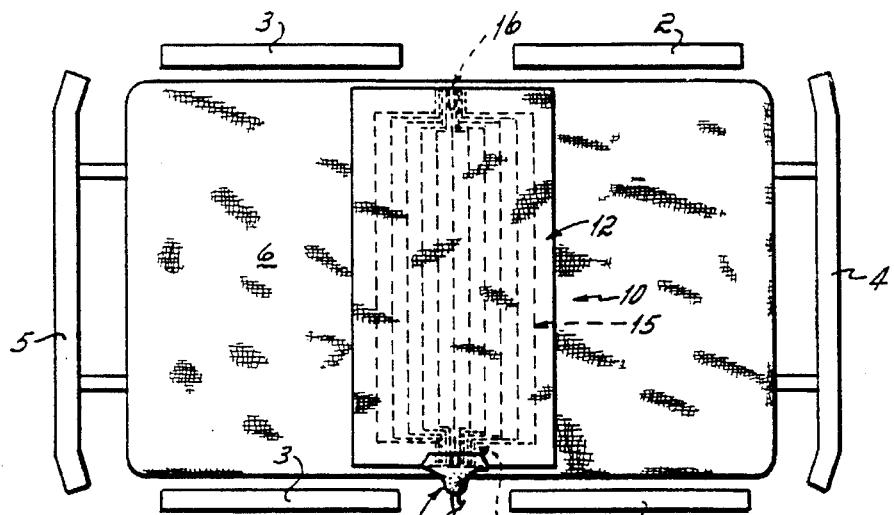
FIG. 1 is a top plan view of a hospital bed with the incontinence detection device of the present invention placed thereon.

Referring first to FIG. 1, there is illustrated a hospital bed 1 which has head side rails 3, foot side rails 3, a headboard 4 and a footboard 5. The bed 1 includes a suitable patient supporting mattress 6. The incontinent detection device 10 of the present invention comprises, generally, a pad 12 placed atop the mattress 6 coupled to appropriate bed electronics (not shown in FIG. 1 but subsequently described) by a tether 13 and clip 14 assembly.

Figure 2:
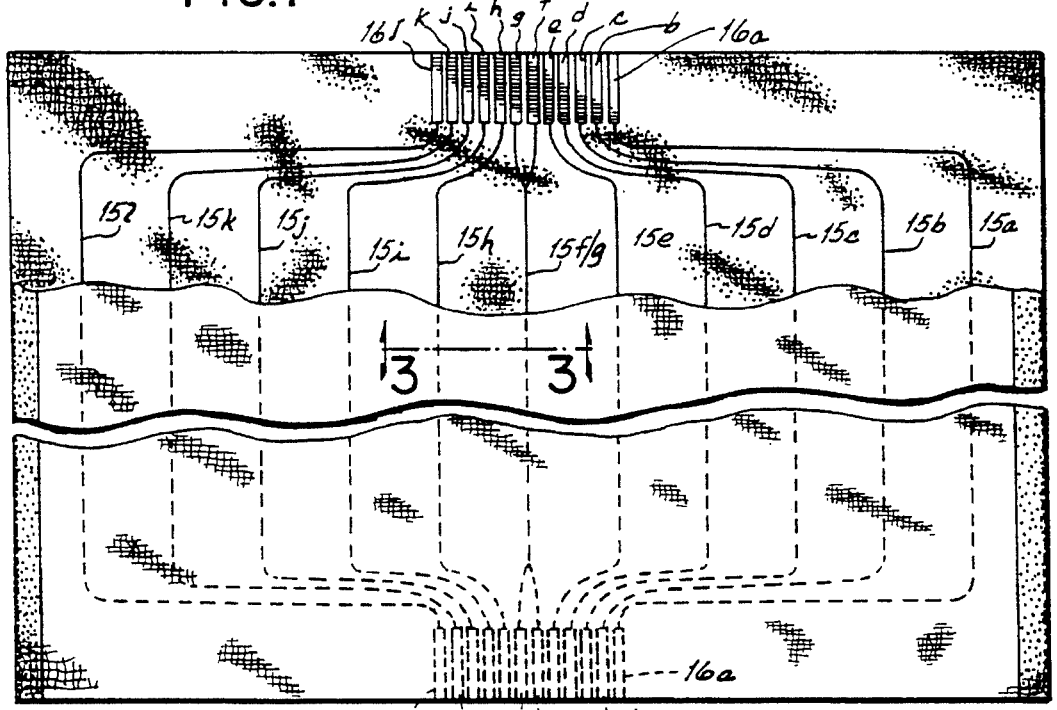
FIG. 2 is a fragmentary top plan view, partially broken away, of the pad with circuits of the present invention.

Referring now to FIG. 2, the pad 12 of the present invention is shown in more detail. The pad 12 is illustrated as being 30"×36" but it can of course be any dimensions which are appropriate. In the illustrated embodiment, the pad 12 includes eleven conductors 15a–e, 15f/g and 15h–l. Each of the conductors 15a–e and 15h–l includes a contact 16a–e and 16h–l, respectively, on either end. Conductor 15f/g includes a pair of contacts 16f and 16g, on either end. The conductors 15a–e, 15f/g and 15h–l are spaced apart by approximately 2.5 inches in the bed longitudinal direction. The conductors 15a–e, 15f/g and 15h–l are approximately straight and parallel within the sensor area of the pad, however, it will be appreciated that the distance between adjacent conductors becomes much smaller as the conductors are curved toward their respective contacts at the edges of the pad.

Figures 3, 3A:
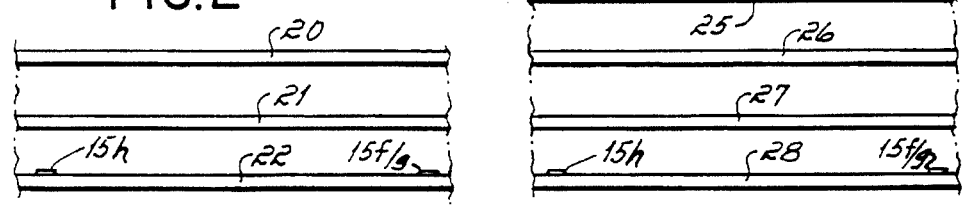
FIG. 3 is a sectional view taken along line 3—3 of FIG. 2 illustrating a disposable pad layup.
FIG. 3A is a view similar to FIG. 3 but illustrating the reusable pad layup.

The pad 12 incorporated within the device 10 of the present invention can be either a disposable pad or a launderable, reusable pad. Referring to FIG. 3, the pad 12 is illustrated in cross section. The pad 12 as illustrated in exploded fashion is a disposable pad manufactured by Stearns Technical Textiles, Cincinnati, Ohio. The disposable pad comprises a top layer 20 of nonwoven fabric, a middle layer 21 of absorbent material, and a bottom layer 22 of water proof backing. The conductors 15a–e, 15f/g and 15h–l are bonded to the backing 22 prior to pad assembly.

Referring to FIG. 3A, a reusable pad 12 is illustrated in exploded cross section. The reusable pad 12 is manufactured by Standard Textile, Cincinnati, Ohio. The pad 12 has an upper layer 25 of 100% brushed polyester, a first middle layer 26 of 50% polyester/50% cotton, a second middle layer 27 of 100% cotton looped absorbent ply, and a bottom layer 28 of vinyl barrier material. The conductors 15a–e, 15f/g, and 15h–l are bonded to the vinyl barrier material 28. An additional source for reusable pad 12 is Stearns Technical Textiles, distributor of Kylie® Health Care Products.

The conductors 15a–e, 15f/g and 15h–l can be fabricated from a number of different materials depending on whether pad 12 is of the disposable type or the reusable type. If the pad 12 is of the disposable type, the conductors can be fabricated of either metallized mylar strips, conductive ink or conductive glue. If the pad 12 is of the reusable type, the conductors can additionally be fabricated of metallized thread. The conductive ink can be manufactured of silver particles mixed into a bonding agent such as a vinyl base ink. One source for such a conductive ink is Olin-Hunt Conductive Materials, Ontario, Calif., product code 7073. The conductive glue can be manufactured of aluminum or silver particles mixed into a water base glue, with copper particles being a less desirable substitute for aluminum and silver.

Figure 4:
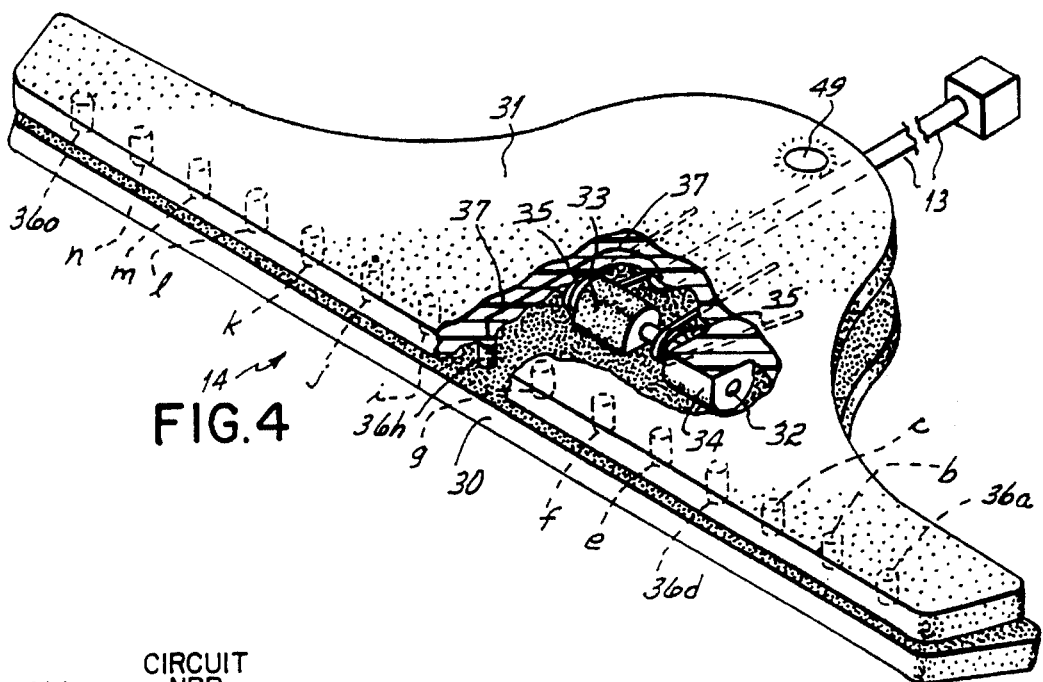
FIG. 4 is a perspective view of the clip which connects the pad of the present invention to the bed electronics.

Referring now to FIG. 4, there is illustrated the clip 14 of present invention which connects the pad 12 to associated bed electronics via an electrical tether or cable 13. The clip 14 includes lower and upper clip halves 30 and 31, which are hinged together via a pin 32. Pin 32 is secured to lower clip half 30 through pin support 33, and is connected to upper clip half 31 through a pair of pin supports on either side of the pin support 33, one of which is shown at 34. A pair of torsion springs 35 maintain the clip halves 30 and 31 in a normally clamped condition. Fifteen contact pins 36a–n are connected to upper clip half 31, each of which is separately electrically wired back to and through the tether 13 as by leads, one of which is shown at 37. Thus, there are 15 potential circuits, as labeled circuit numbers C1–C15 in FIG. 6. The number of clip pins 36a–n exceeds the number of pad contacts 16a–l by three. Thus, clip 14 is able to accommodate some misalignment with the pad contacts 16a–l while insuring that all of the pad contacts 16a–l are connected to the bed electronics.

Figure 6:
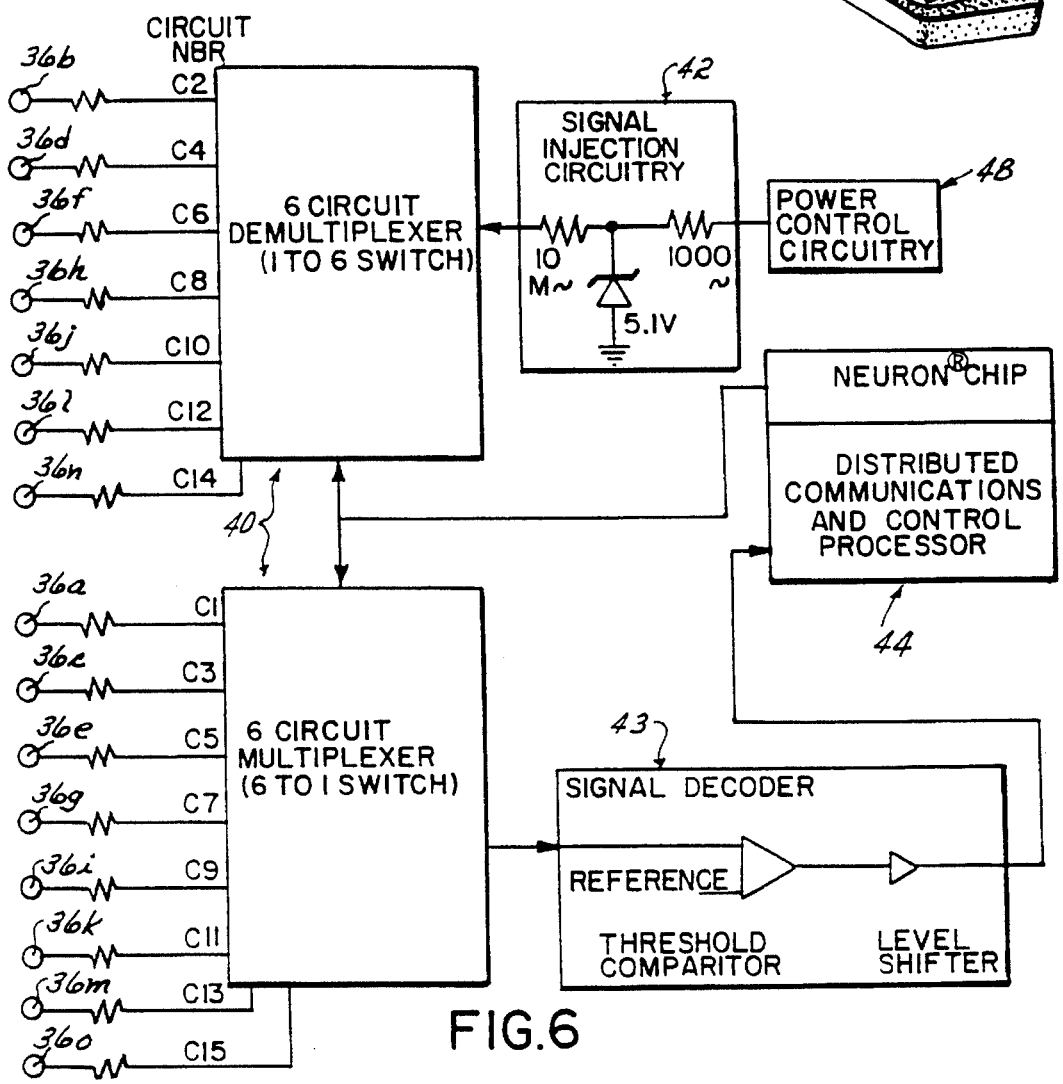
FIG. 6 is a detailed block diagram of the signal injection, multiplexer/demultiplexer, and signal decoder of FIG. 5.
Figure 5:
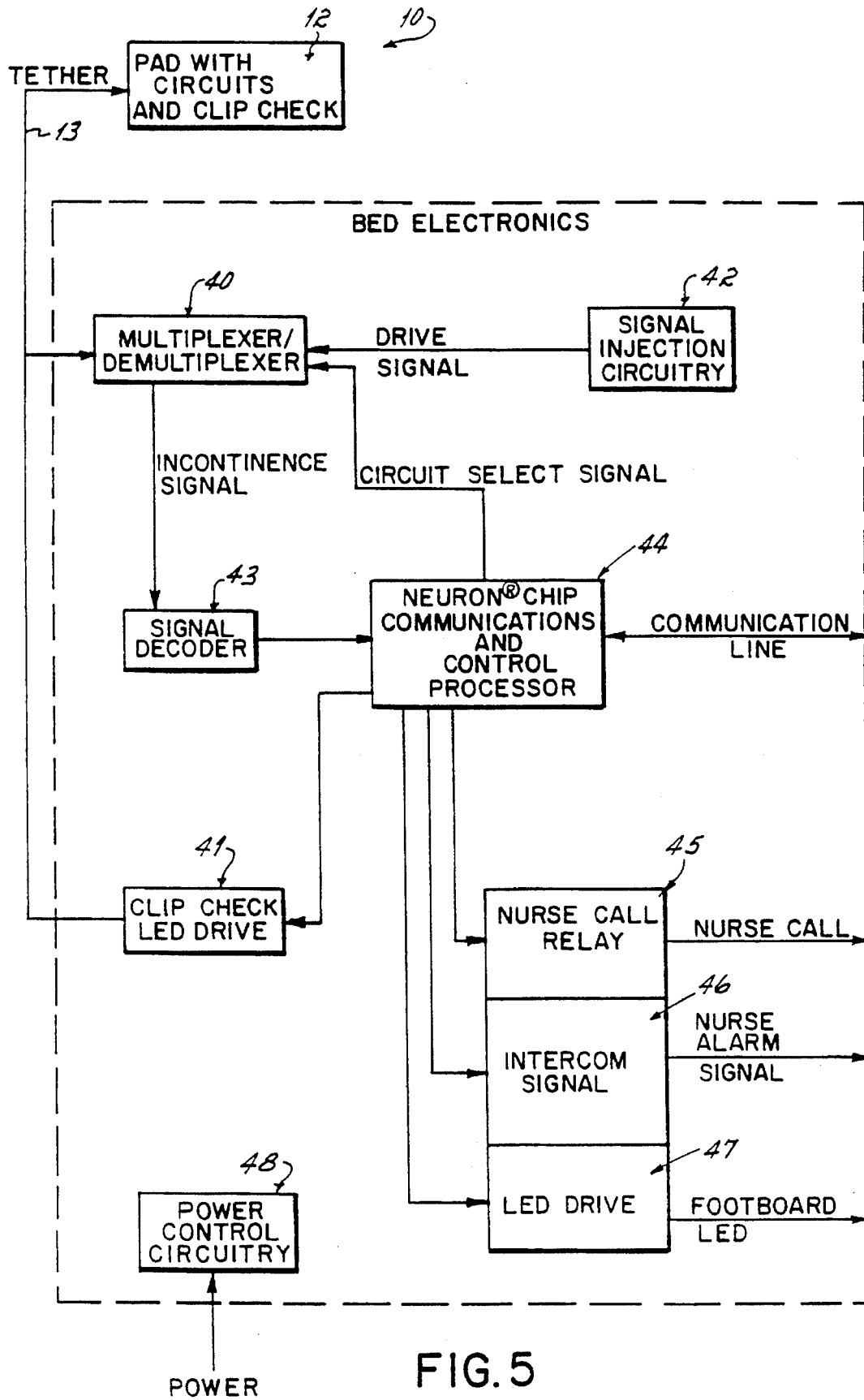
FIG. 5 is a block diagram of the electronics associated with the pad and the bed.

With reference now to FIG. 5, the incontinence detection system block diagram is illustrated. The pad 12 is tethered via tether 13 to a multiplexer/demultiplexer 40 and a clip check LED drive 41. The multiplexer/demultiplexer 40 accepts drive signals from signal injection circuitry 42 and circuit select signals from a communications and control processor 44, a Neuron® chip, manufactured by Echelon Corporation. The multiplexer/demultiplexer 40 sends an incontinent signal to the signal decoder 43 which in turn sends a signal to the communications and control processor 44. The processor 44 can send signals to a nurse call relay 45 for a nurse call, to an intercom signal 46 for generating a nurse alarm LO signal or to a LED drive 47 for generating a LED signal at the bed footboard. Power is supplied to power control circuitry 48 which after providing the first level of patient protection, distributes the necessary power to the other circuitry. In FIG. 6, the signal injection circuitry 42, multiplexer/demultiplexer 40 and signal decoder 43 blocks are shown in more detail.

Referring now to FIGS. 2 and 4–6, the operation of the present invention will be described. The pad 12 is first placed atop the hospital bed, and the tether 13 is connected to the hospital bed electronics. Clip 14 is then applied to one of the sides of the pad 12, while visually aligning the pins 36a–o with the pad contacts 16a–l. In order to ensure that the clip 14 is properly aligned with the contacts 16a–l, and to ensure that all of the contacts 16a–l are connected to the bed electronics via the clip 14, the processor 44 sends a circuit select signal to the multiplexer/demultiplexer 40 which in turn applies voltage first to pin 36f and the processor 44 checks for continuity to pin 36g. Next voltage is applied to pin 36h and the processor 44 checks for continuity to pins 36g and 36i. Finally voltage is applied to pin 36j and the processor checks for continuity to pin 36i. The purpose of this sequence is for the processor 44 to locate the short resulting from contacts 16f and 16g being connected to the same conductor 15f/g, and then to initialize the locations of clip pins 36a–n relative to conductor 15f/g. From this information the processor 44 can determine if the clip 14 has been properly connected to the pad 12 such that all contacts 16a–l are connected to the bed electronics and which pins 36a–o in the clip 14 are connected to which contacts 16a–l in the pad 12. If all contacts 16a–l are successfully connected to twelve of the pins 36a–o, the processor 44 sends a signal to the clip check LED drive 41 which causes an LED 49 on the clip 14 to light indicating that alignment has been achieved.

The incontinence detection, system of the present invention can operate in one of two ways. Voltage can be applied sequentially to each contact 16a–l (corresponding to circuit numbers 1–12, FIG.6, assuming pins 36a–l are paired with contacts 16a–l and hence conductors 15a–e, 15f/g and 15e–l respectively) and the next adjacent contact can be checked for continuity. Thus, voltage is applied and continuity is checked for eleven separate circuits. Since the circuits have a linear spacing of approximately 2.5" and since that spacing corresponds to a predetermined liquid volume of approximately 20cc's (20cc liquid volume creates a moistened pad circular area having approximately a 2.5" diameter), the resolution of the device 10 is thus 20cc's with the device being able to determine the liquid volume of an incontinent event from approximately 20cc's up to approximately 400–700cc's (full pad). While the circuits have a linear spacing of approximately 2.5", the volume of liquid required to contact successive lines increases at an ever increasing rate, and hence the relationship is nonlinear. In fact, it is believed that the relationship is exponential. Thus, while 3 shorted circuits would indicate a moistened circular area of approximately 7.5" diameter, the liquid volume of the incontinent event would likely be more than three times the volume at 2.5 ", or 60cc, and would be closer to approximately 100cc. Test results indicate that one shorted circuit with spacing of 2.5" equals approximately 20cc's, two adjacent shorted circuits of spacing 5" equals approximately 45cc's, three adjacent shorted circuits of 7.5" spacing equals approximately 100cc's, and four adjacent shorted circuits of spacing 10" equals approximately 160cc's, with the pad completely full of liquid being approximately 400–700cc's. Should the sensed shorted circuits not be adjacent, however, this non-linear relationship would not hold for the total liquid volume in the pad. For example, assuming three shorted circuits were sensed, each with a spacing of 2.5", but none of which were adjacent, the total would be 3×20cc's or approximately 60cc's, rather than 100cc's in the event that all three shorted circuits were adjacent one another. As the incontinence detection device of the present invention has the capability to note the relationship of each of the circuits to each of the other circuits, both of the above two different methods of totalling the liquid volume within the pad, on the basis of the relationship between the shorted circuits, are within the scope of the present invention.

Describing more particularly this method of operation of the invention, the processor 44 sends a circuit select signal to the multiplexer/demultiplexer 40, initially applying voltage from the signal injection circuitry 42 to pad conductor 15b via contact 16b. Pad conductors 15a and 15c are then checked for signal presence (continuity to conductor 15b of the pad 12) via contacts 16a and 16c respectively. This check is accomplished by first connecting pad conductor 15a to the signal decoder 43 which then signals the processor 44 as to whether or not there is continuity, then repeating the process for pad conductor 15c. The multiplexer/demultiplexer 40 then sends an incontinence signal to the signal decoder 43 based on whether there was continuity between the two circuits checked. If the pad 12 was moistened such that the moistened pad completed the circuit between, for example, conductors 15a and 15b, then upon the voltage being applied to the clip pin 36a–o corresponding to conductor 15b and contact 16b, current would flow through conductor 15b across the moistened pad 12 through conductor 15a and contact 16a and back to the multiplexer 40 through the clip pin 36a–o corresponding to conductor 15a and contact 16a. Thus, the signal decoder 43 would signal the processor 44 that a moistened area of at least a diameter of 2.5 inches was detected between conductors 15a and 15b.

The processor 44 then proceeds to check the remaining combinations of pairs of conductors 15a–l for moistened areas. For example, next a signal is injected into conductor 15d via contact 16d and conductors 15c and 15e via contacts 16c and 16e respectively are checked for continuity. The processor 44 continues to check across the pad injecting signals into conductor 15f via contact 16f with checks to conductors 15e and 15g via contacts 16e and 16grespectively; into conductor 15h via contact 16h with checks to conductors 15g and 15i via contacts 16gand 16i respectively; into conductor 15j via contact 16j with checks to conductors 15j and 15k via contacts 16j and 16k respectively; and finally into conductor 15l via contact 16l with a single check to conductor 15k via contact 16k. The resulting incontinent signal for each of the circuit checks is sent to the signal decoder 43 which in turn sends a signal to the processor 44. The processor 44 now uses this information to determine the size of the moistened pad area and to signal the nurse to report that an incontinent event has occurred, that the pad 12 is full of liquid and needs to be replaced, and/or the liquid volume of the incontinent event based on the size of the moistened area of the pad 12. The processor 44 can then send an appropriate signal to either the nurse call relay 45, intercom signal 46 or LED drive 47 as is desired or has been programmed, providing a caregiver with the information of presence or absence of an incontinent event and volume of the event.

In the other method of operation of the present invention, the linear dimension across which circuits are checked for continuity is 7.5" which corresponds to the distance defined between every four conductors. As discussed in connection with the first embodiment, this linear distance or diameter of moistened pad area corresponds to a liquid volume of approximately 100cc, due to the nonlinear relationship of liquid volume to diameter of moistened pad area. In this embodiment of the invention, and referring now to FIGS. 2 and 4–7, certain ones of the circuits are shorted together within the hardware such that continuity is checked across resulting circuits which have the 7.5" spacing.

Figure 7:
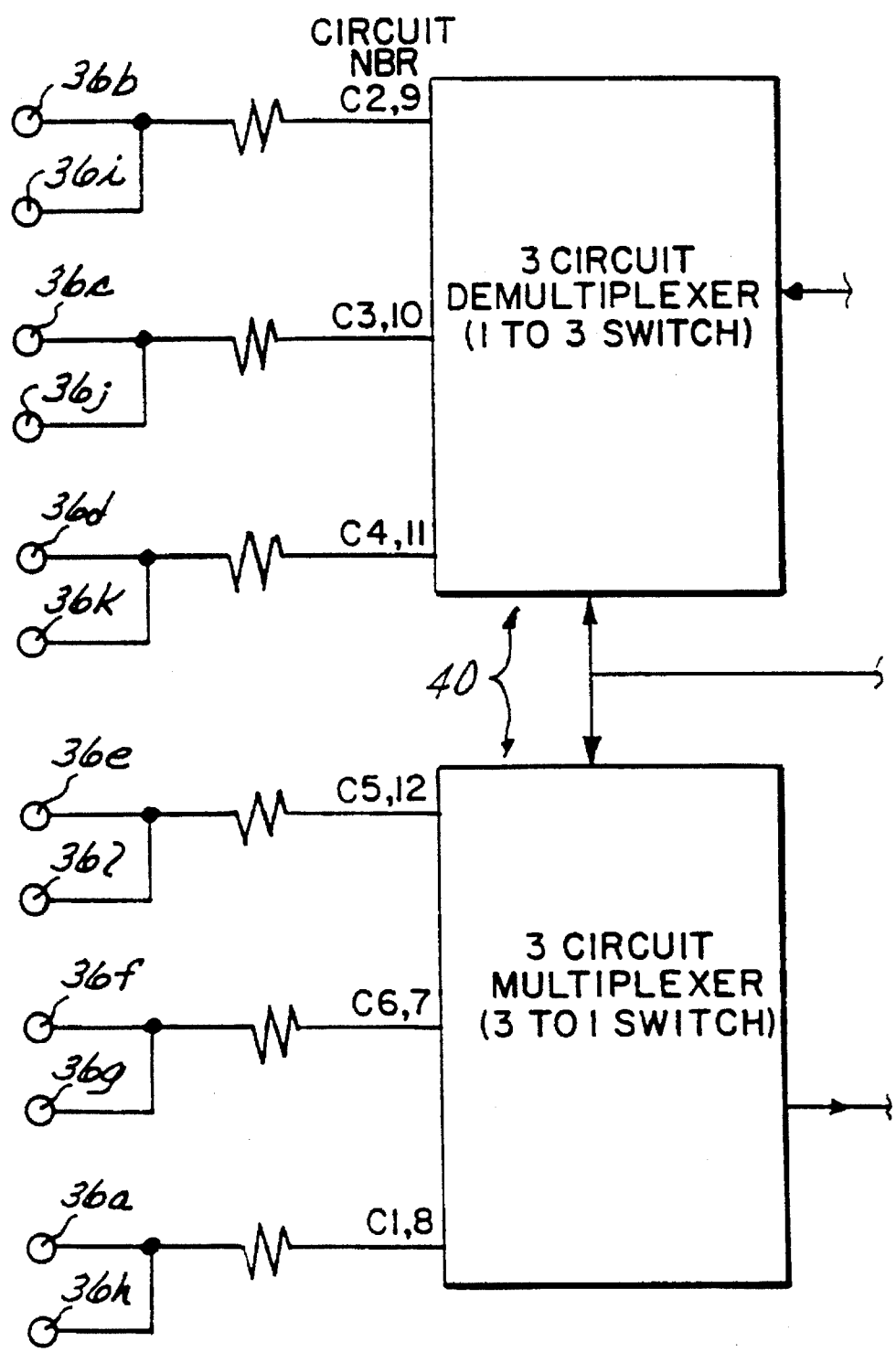
FIG. 7 is the multiplexer/demultiplexer employed in another embodiment of the present invention.

Specifically, and referring particularly to FIG. 7, circuits C2 and C9 corresponding to conductors 15b and 15i, circuits C3 and C10 corresponding to conductors 15c and 15j and circuits C4 and C11 corresponding to conductors 15d and 15k are shorted together for signal injection from the multiplexer/demultiplexer 40, which in this embodiment is a 3–1 and 1–3 switch (assuming pins 36a–l are paired with contacts 16a–l and hence conductors 15a–e, 15f/g and 15e–l respectively). On the multiplexer side, circuits C5 and C12 corresponding to conductors 15e and 15l, circuits C6 and C7 corresponding to conductor 15f/g and circuits Cl and C8 corresponding to conductors. 15a and 15h are likewise shorted within the hardware.

Voltage is applied first to conductors 15b and 15i via their respective contacts 16b and 16i and their associated clip pins, and conductors 15e and 15l are checked for continuity through their respective contacts 16c and 16l and their associated clip pins. Next, voltage is applied to conductors 15c and 15j through contacts 16c and 16j and their associated clip pins and conductor 15f/g is checked via contacts 16f and 16gand their associated clip pins. Lastly, voltage is applied to conductors 15d and 15k via contacts 16d and 16k and their associated clip pins and conductors 15a and 15h via contacts 16a and 16h and their associated clip pins are checked for continuity. As in the prior embodiment, the resulting incontinent circuit check sends a signal to the signal decoder 43 which in turn sends a signal to the processor 44. The processor 44 can then send an appropriate signal to either the nurse call relay 45, intercom signal 46 or LED drive 47 as is desired, or has been programmed, providing a care giver with the information indicating presence or absence of an incontinent event and volume of the event. In this embodiment, it will be appreciated that if the circuits for which continuity is checked did not overlap, rather large moistened pad areas could go completely undetected. For example, if voltage is applied to conductor 15f/g and conductors 15c and 15i were checked for continuity, with no subsequent overlapping circuits checked for continuity, a moistened area having a diameter of approximately 15 inches could potentially go undetected. Therefore, by having the circuits for which continuity is checked overlap by approximately 5 inches, moistened pad areas having diameters of approximately 7.5–10 inches are detectable.

In the operation of either embodiment, the communication line illustrated in FIG. 5 may be used when a communication network is available, in lieu of the nurse call, nurse alarm and footboard LED. Furthermore, the present invention is ideally suited for use in conjunction with the nurse call system of co-pending application Ser. No. 08/090,804, filed Jul. 12, 1993, entitled Improved Patient/Nurse Call System and assigned to the assignee of the present invention, the entire substance of which is hereby incorporated by reference herein.

Those skilled in the art will readily recognize numerous adaptations and modifications which can be made to the present invention which will result in an improved incontinence detection device, yet all of which will fall within the spirit and scope of the present invention as defined in the claims. For example, the incontinence detection device could be incorporated into an adult brief or other incontinence products. Accordingly, the invention is to be limited only by the scope of the following claims and their equivalents.

What is claimed is:

1. Apparatus for detecting a patient incontinent event and corresponding liquid volume of the event comprising:

a pad;

a plurality of electrical circuits on said pad, said circuits being spaced on said pad, each of said circuits having spaced apart conductors defining a linear dimension across a respective one of said circuits, said linear dimension having a correlation to a predetermined liquid volume of an incontinent event;

a power source; and a controller for applying power source voltage to and checking continuity of said spaced circuits and totalling the number of circuits which are shorted by liquid volume connecting the spaced apart conductors of the circuit;

whereby when an incontinent event occurs said controller indicates to a care provider that an incontinent event has occurred and the liquid volume of the event.

2. The apparatus of claim 1 wherein said predetermined liquid volume corresponds to the liquid volume of a minimum threshold incontinent event desired to be detected.

3. The apparatus of claim 1 wherein said spaced apart conductors of the plurality of circuits are overlapped on the pad.

4. The apparatus of claim 3 wherein said linear dimension is about 7.5 in.

5. The apparatus of claim 3 wherein said predetermined liquid volume is about 100cc.

6. The apparatus of claim 1 wherein said spaced circuits are contiguous.

7. The apparatus of claim 6 wherein said linear dimension is about 2.5 in.

8. The apparatus of claim 6 wherein said predetermined liquid volume is about 20cc.

9. The apparatus of claim 1 wherein said pad is disposable.

10. The apparatus of claim 9 wherein said circuits are fabricated of metallized mylar strips.

11. The apparatus of claim 9 wherein said circuits are fabricated of conductive ink.

12. The apparatus of claim 9, wherein said circuits are fabricated of conductive glue.

13. The apparatus of claim 1 wherein said pad is reusable.

14. The apparatus of claim 13 wherein said circuits are fabricated of metallized mylar strips.

15. The apparatus of claim 13 wherein said circuits are fabricated of conductive ink.

16. The apparatus of claim 13 wherein said circuits are fabricated of conductive glue.

17. The apparatus of claim 13 wherein said circuits are fabricated of metallized thread.

18. Apparatus for detecting a patient incontinent event and corresponding liquid volume of the event comprising:

a pad;

a plurality of electrical circuits on said pad, each of said circuits having spaced apart conductors defining a linear dimension across a respective one of said circuits, said spaced apart conductors of the plurality of circuits being overlapped on the pad, said linear dimension having a correlation to a predetermined liquid volume of a minimum threshold incontinent event desired to be detected;

a power source; and a controller for serially applying power source voltage to and checking continuity of adjacent ones of said spaced circuits and totalling the number of circuits which are shorted by liquid volume connecting the spaced apart conductors of the circuit;

whereby when an incontinent event occurs said controller indicates to a care provider that an incontinent event has occurred and the liquid volume of the event.

19. Apparatus for detecting a patient incontinent event and corresponding liquid volume of the event comprising:

a pad;

a plurality of electrical circuits on said pad, said circuits being spaced on said pad in contiguous fashion, each of said circuits having spaced apart conductors defining a linear dimension across a respective one of said circuits, said linear dimension having a correlation to a predetermined liquid volume of a minimum threshold of an incontinent event desired to be detected;

a power source; and a controller for serially applying power source voltage to and checking continuity of adjacent ones of said spaced circuits and totalling the number of circuits which are shorted by liquid volume connecting the spaced apart conductors of the circuit;

whereby when an incontinent event occurs said controller indicates to a care provider that an incontinent event has occurred and the liquid volume of the event.

20. Apparatus for detecting a patient incontinent event and corresponding liquid volume of the event comprising:

a pad;

a plurality of electrical circuits on said pad, said circuits being spaced on said pad, each of said circuits having spaced apart conductors defining a linear dimension across a respective one of said circuits, said linear dimension having a correlation to a predetermined liquid volume of an incontinent event;

a power source; and a controller for applying power source voltage to and checking continuity of said spaced circuits and totalling the number of circuits which are shorted by liquid volume connecting the spaced apart conductors of the circuit;

whereby when an incontinent event of a predetermined minimum threshold liquid volume occurs said controller indicates to a care provider that an incontinent event of a liquid volume at least as great as said predetermined minimum threshold liquid volume has occurred.

21. Apparatus for detecting a patient incontinent event and corresponding liquid volume of the event comprising:

a pad;

a plurality of electrical circuits on said pad, said circuits being spaced on said pad, each of said circuits having spaced apart conductors defining a linear dimension across a respective one of said circuits, said linear dimension having a correlation to a predetermined liquid volume of an incontinent event;

a power source; and a controller for applying power source voltage to and checking continuity of said spaced circuits and totalling the number of circuits which are shorted by liquid volume connecting the spaced apart conductors of the circuit;

whereby when an incontinent event of a predetermined maximum liquid volume occurs, as indicated by detection of a predetermined number of shorted circuits by the controller, said controller indicates to a care provider that an incontinent event of a liquid volume at least as great as said predetermined maximum liquid volume has occurred.

* * * * *